US00PP15623P2

(12) United States Plant Patent
Endisch

(10) Patent No.: US PP15,623 P2
(45) Date of Patent: Mar. 1, 2005

(54) ***GERANIUM* PLANT NAMED 'GENFIVIO'**

(50) Latin Name: *Pelargonium×hortorum*
Varietal Denomination: Genfivio

(75) Inventor: Gerd Endisch, Hagenbach (DE)

(73) Assignee: Willi Endisch GbR, Hagenbach (DE)

( * ) Notice: Subject to any disclaimer, the term of this patent is extended or adjusted under 35 U.S.C. 154(b) by 11 days.

(21) Appl. No.: 10/847,104

(22) Filed: May 17, 2004

(51) Int. Cl.[7] ..... A01H 5/00
(52) U.S. Cl. ..... Plt./329
(58) Field of Search ..... Plt./329

(56) References Cited

U.S. PATENT DOCUMENTS

PP14,210 P2 * 10/2003 Hofmann ..... Plt./329

* cited by examiner

*Primary Examiner*—Kent Bell
*Assistant Examiner*—W C Haas
(74) *Attorney, Agent, or Firm*—Mark P. Bourgeois

(57) ABSTRACT

A new and distinct cultivar of *Geranium* plant named 'Genfivio' that is characterized by semi-double purple red flowers, medium green foliage and an early to medium flower response.

1 Drawing Sheet

Botanical classification: *Pelargonium×hortorum.*
Variety denomination: 'Genfivio'.

BACKGROUND OF THE INVENTION

The present invention relates to a new and distinct cultivar of *Geranium* plant botanically known as *Pelargonium× hortorum* and hereinafter referred to by the cultivar name 'Genfivio'.

The new cultivar is the product of a breeding program conducted by the inventor in a cultivated area of Hagenbach, Germany. The objective of the breeding program is to develop new *Geranium* cultivars that are early flowering with semi-double flowers and medium green foliage.

'Genfivio' is a hybrid that originated from the induced hybridization of the female or seed parent a proprietary selection of *Pelargonium×hortorum* identified by number G367 (not patented) and the male or pollen parent a proprietary selection of *Pelargonium×hortorum* identified by number F345 (not patented). The cultivar 'Genfivio' was selected by the inventor in 2000 as a single plant within the progeny of the stated cross in a controlled environment of Hagenbach, Germany.

Asexual reproduction by terminal cuttings of the new cultivar 'Genfivio' were taken in 2000 in Hagenbach, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Geranium* cultivar 'Genfivio'. These traits in combination distinguish 'Genfivio' as a new and distinct cultivar apart from other known existing varieties of *Geranium.*

1. *Geranium* 'Genfivio' exhibits purple red flowers.
2. *Geranium* 'Genfivio' exhibits semi-double flowers.
3. *Geranium* 'Genfivio' exhibits medium green foliage.

4. *Geranium* 'Genfivio' exhibits an early to medium flower response.

The closest comparison variety is *Geranium* 'Pacshovi' (U.S. Plant Pat. No. 14,210). 'Genfivio' is different than 'Pacshovi' in having flowers that are more purple and having lighter red pedicels.

The new cultivar 'Genfivio' is distinguishable from the female parent *Geranium* proprietary selection G367 by the following characteristics:

1. 'Genfivio' has purple red flowers. The flowers of G367 are more red.
2. 'Genfivio' does not have a zonation pattern.

The new cultivar 'Genfivio' is distinguishable from the male parent *Geranium* proprietary selection F345 by the following characteristics:

1. 'Genfivio' has purple red flowers. The flowers of F345 are more red.
2. 'Genfivio' does not have a zonation pattern.

BRIEF DESCRIPTION OF THE DRAWING

The accompanying photograph illustrates the distinguishing traits of *Geranium* 'Genfivio'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Geranium* cultivar named 'Genfivio'. Data was collected in Hagenbach, Germany from 12 week old plants grown under glass greenhouse conditions. The plants were grown in 12 cm diameter containers. The time of year was Spring and the daytime temperature ranged from 18 to 26° Centigrade. The temperature at night ranged from 16 to 20° Centigrade. The light level was 20 to 35 klux. No photoperiodic treatments were used. The growth retardant Cycocel 720 was applied at a rate of 0.05 percent. Color determinations are in accordance with The Royal Horticultural Society Colour Chart 2001 edition, except where general color terms of ordinary dictionary significance are used. The growing requirements are similar to the species.

'Genfivio' has not been tested under all possible conditions and phenotypic differences may be observed with variations in environmental, climatic, and cultural conditions, however, without any variance in genotype.

Botanical classification: *Pelargonium×hortorum* cultivar 'Genfivio'.
Annual or perennial: Annual.
Parentage: 'Genfivio' is a hybrid plant that resulted from the induced hybridization of the following parent plants:
*Female parent*.—A proprietary selection of *Pelargonium×hortorum* identified by number G367.
*Male parent*.—A proprietary selection of *Pelargonium×hortorum* identified by number F345.
Vigor: Moderate.
Growth rate: Approximately 6 cm. per month.
Growth habit: Upright, outwardly spreading.
Plant shape: Globose.
Plant height: Average 20 cm. in height.
Plant width: Average 18 cm. in width.
Suitable container size: 10 to 14 cm containers.
Propagation: Terminal cuttings.
Time to initiate roots: Approximately 5–7 days to produce roots on an initial cutting.
Time to produce a rooted cutting or liner: Approximately 20–24 days.
Crop time: From a rooted cutting, approximately 12.5 weeks are required to produce a finished flowering plant.
High temperature tolerance: 40 degrees Centigrade.
Low temperature tolerance: 0 degrees Centigrade.
Root system: Fine and fibrous.
Stem:
*Branching habit*.—Free branching.
*Basal branching*.—Yes.
*Average number of lateral branches*.—6.
*Pinching*.—No.
*Lateral branch dimensions*.—11 cm. in length and 1 cm. in diameter.
*Lateral branch strength*.—Moderately strong.
*Color*.—143B.
*Texture*.—Fine pubescence is present.
*Internode length*.—2.5 cm. between nodes.
*Shape*.—Round.
Foliage:
*Leaf arrangement*.—Alternate.
*Compound or single*.—Single.
*Quantity of leaves per lateral branch*.—5.
*Leaf shape*.—Reniform.
*Leaf apex*.—Rounded.
*Leaf base*.—Cordate.
*Leaf length*.—6 cm. in length.
*Leaf width*.—9.5 cm. in width.
*Texture*.—Fine pubescence is present on both the upper and lower leaf surfaces.
*Leaf margin*.—Bicrenate.
*Vein pattern*.—Pinnate.
*Young leaf color* (*upper surface*).—144A.
*Young leaf color* (*lower surface*).—144B.
*Mature leaf color* (*upper surface*).—137A to 137B.
*Mature leaf color* (*lower surface*).—137C.
*Vein color* (*upper surface*).—144B.
*Vein color* (*lower surface*).—144D.
*Zonation pattern*.—Not present.
*Leaf attachment*.—Petiolate.
*Petiole dimensions*.—7.5 cm. in length and 3.0 mm. in width.
*Petiole color*.—144A.
*Petiole texture*.—Fine pubescence is present.
Stipules:
*Stipule dimensions*.—0.8 cm in length and 1.2 cm in width.
*Stipule color*.—143C.
Inflorescence:
*Inflorescence arrangement*.—Rounded hemispherical umbels.
*Inflorescence type*.—Umbel.
*Inflorescence dimensions*.—4.5 cm in height and 6.5 cm in width.
*Flowering habit*.—Continuous.
*Quantity of flowers per inflorescence*.—Approximately 6.
*Quantity of buds per lateral stem*.—Approximately 18.
*Quantity of flowers and buds per plant*.—Approximately 160.
*Flowering season*.—Spring to Summer.
*Time to flower*.—Approximately 8 weeks.
*Rate of flower opening*.—Approximately 25% of the flowers are opened at once.
*Fragrance*.—None.
*Bud dimensions*.—6 mm. in length and 3.8 mm. in diameter.
*Bud shape*.—Elliptic.
*Bud color*.—143B.
*Rate of bud opening*.—4 days.
*Flower aspect*.—Upright.
*Flower shape*.—Shallow cup shaped, rounded, semi-double.
*Flower dimensions*.—5.3 cm. in diameter and 1.5 cm. in height.
*Flower longevity*.—Lasts approximately 10 days on plant.
*Petal texture*.—Glabrous.
*Number of petals*.—Six in number.
*Petals fused or unfused*.—Unfused.
*Petal shape*.—Ovate.
*Petal margin*.—Entire.
*Petal apex*.—Rounded.
*Petal base*.—Attenuate.
*Petal dimensions*.—2.4 cm. in length and 2.1 cm. in width.
*Upper petal color when opening* (*upper side*).—N66B with a margin N66A, white area at base, 2 mm in length and 1.5 mm in width, color 155B and two markings above white area, 3 mm in length and 1 mm in width, color 67A.
*Lower petal color when opening* (*upper side*).—N66B with a margin 66A.
*Upper petal color when opening* (*under side*).—N66B with a margin N66A, white area at base, 2 mm in length and 1.5 mm in width, color 155B.
*Lower petal color when opening* (*under side*).—71D with a margin 66A.
*Upper petal color fully opened* (*upper side*).—N66B with a margin N66A, white area at base, 2 mm in length and 1.5 mm in width, color 155B and two markings above white area, 3 mm in length and 1 mm in width, color 67A.

*Lower petal color fully opened* (*upper side*).—N66B with a margin 66A.
*Upper petal color fully opened* (*under side*).—N66B with a margin N66A, white area at base, 2 mm in length and 1.5 mm in width, color: 155B.
*Lower petal color fully opened* (*under side*).—71D with a margin 66A.
*Petaloids*.—Variable in quantity, size and shape.
*Petaloid color*.—N66B.

Self-cleaning or persistent: Persistent.

Sepals:
*Number of sepals*.—5.
*Sepal surface*.—Upper side: dull and pubescent, Lower side: glabrous.
*Sepal shape*.—Lanceolate.
*Sepal margin*.—Entire.
*Sepal apex*.—Acute.
*Sepal base*.—Cuneate.
*Sepal dimensions*.—1.0 cm. in length and 2.5 mm. in width.
*Sepal color immature* (*upper side*).—143B.
*Sepal color immature* (*under side*).—143B.
*Sepal color mature* (*upper side*).—143B with light red at the base.
*Sepal color mature* (*under side*).—143B.

Peduncle:
*Peduncle dimensions*.—8.0 cm. in length and 3.0 mm. in diameter.
*Peduncle angle*.—15°.
*Peduncle color*.—144A.
*Peduncle strength*.—Moderate.
*Peduncle texture*.—Fine pubescence is present.

Pedicels:
*Pedicel dimensions*.—2.1 cm. in length and 1.2 mm. in diameter.
*Pedicel angle*.—45°.
*Pedicel color* (*young*).—143A.
*Pedicel color* (*mature*).—46B.
*Pedicel strength*.—Moderate.
*Pedicel texture*.—Fine pubescence is present.

Reproduction organs:
*Stamen number*.—6.
*Anther shape*.—Ovate.
*Anther dimensions*.—2 mm.
*Anther color*.—61B.
*Amount of pollen*.—Moderate.
*Pollen color*.—31A.
*Pistil number*.—1 in number.
*Pistil dimensions*.—8 mm. in length.
*Stigma shape*.—Five parted, star shaped.
*Stigma color*.—46A.
*Style length*.—5 mm.
*Style color*.—46A.
*Ovary color*.—143B.

Seed: Seed production has not been observed.

Disease and pest resistance: Plants of the new *geranium* have not been observed for disease or pest resistance.

It is claimed:

1. A new and distinct variety of *Geranium* plant named 'Genfivio' as described and illustrated.

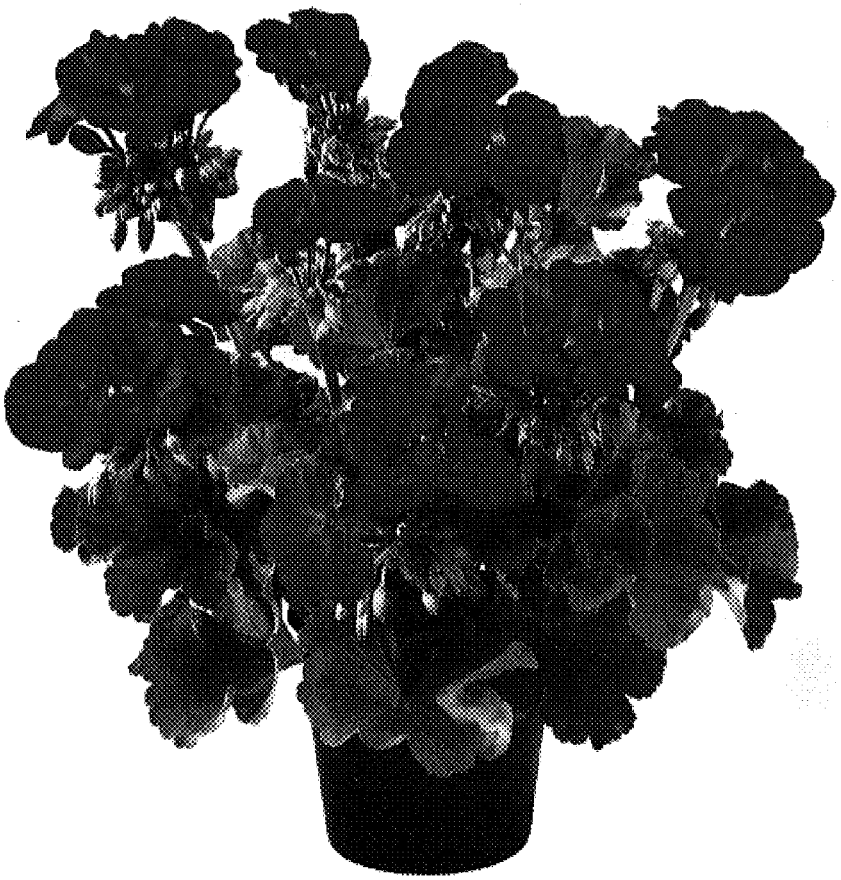

* * * * *